United States Patent
Hoffman

(10) Patent No.: US 7,559,946 B2
(45) Date of Patent: Jul. 14, 2009

(54) APPARATUS FOR INSERTION INTO A BODY LUMEN

(75) Inventor: Steven William Hoffman, N. Olmsted, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 848 days.

(21) Appl. No.: 10/803,245

(22) Filed: Mar. 18, 2004

(65) Prior Publication Data

US 2004/0204718 A1   Oct. 14, 2004

Related U.S. Application Data

(60) Provisional application No. 60/455,642, filed on Mar. 18, 2003.

(51) Int. Cl.
  *A61F 2/06* (2006.01)
  *A61B 10/00* (2006.01)
  *A61D 1/12* (2006.01)
(52) U.S. Cl. .................. 623/1.11; 600/564; 606/106
(58) Field of Classification Search ............ 606/108, 606/110, 205, 207, 170, 174, 106; 623/9, 623/1.11; 600/562, 564
See application file for complete search history.

(56) References Cited

U.S. PATENT DOCUMENTS 5,295,990 A * 3/1994 Levin ................. 606/49
5,725,532 A * 3/1998 Shoemaker .......... 623/1.11
5,755,723 A * 5/1998 Lombardo ........... 606/170
5,928,263 A * 7/1999 Hoogeboom ......... 606/205
6,136,006 A   10/2000 Johnson et al.
6,261,308 B1 * 7/2001 Saavedra ............. 606/207
7,105,016 B2 * 9/2006 Shiu et al. ........... 623/1.12

* cited by examiner

*Primary Examiner*—Todd E Manahan
*Assistant Examiner*—Victor X Nguyen
(74) *Attorney, Agent, or Firm*—Tarolli, Sundheim, Covell & Tummino LLP

(57) ABSTRACT

An apparatus (10) for insertion into a body lumen (16) includes an elongate member (30) having a proximal end (32) and a distal end (34) insertable into the body lumen (16). At least one clamping arm (100) includes a first end (102) having a pivotal connection with the distal end (34) of the elongate member (30). The pivotal connection provides pivotal movement of the at least one clamping arm (100) relative to the elongate member (30). The at least one clamping arm (100) extends away from the pivotal connection toward the proximal end (32) of the elongate member (30). The apparatus (10) also includes a control mechanism (40) for controlling the pivotal movement of the at least one clamping arm (100) relative to the elongate member (30). The apparatus (10) may also include an assembly (150) for controlling advancement of the member (30) in the body lumen (16).

3 Claims, 6 Drawing Sheets

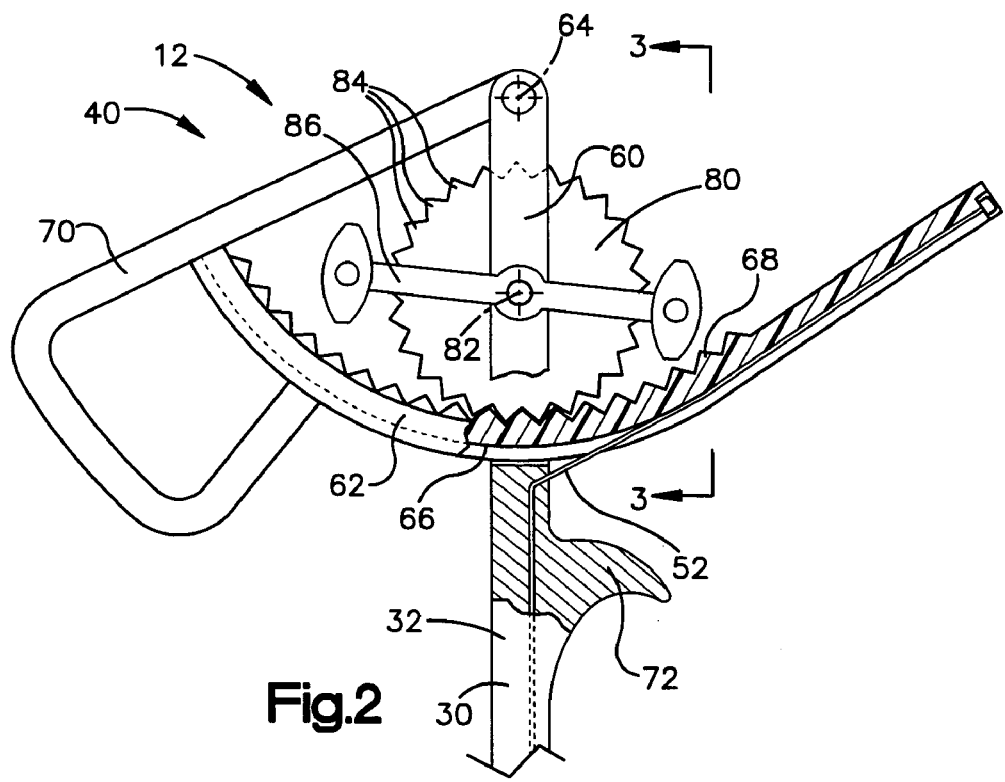
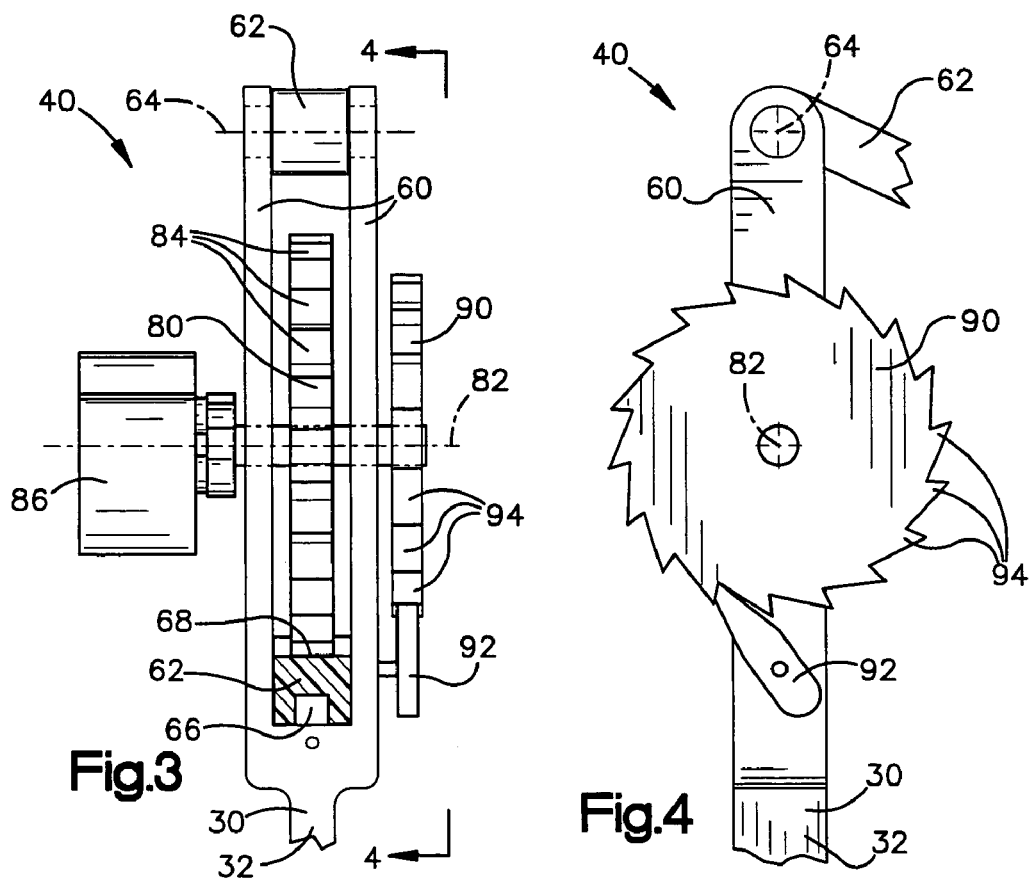

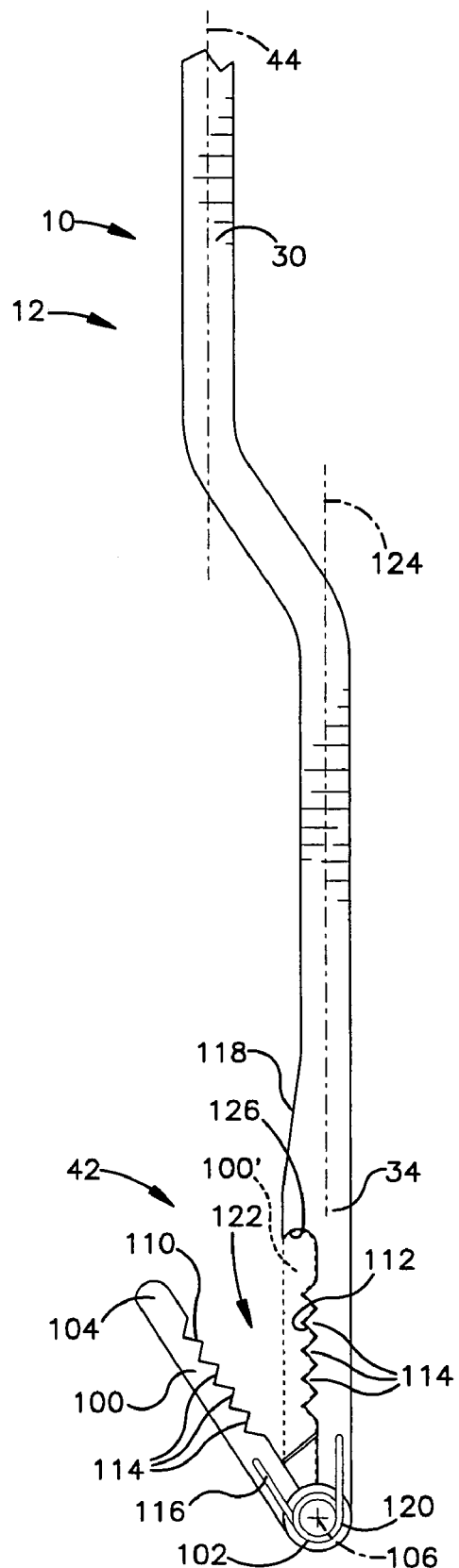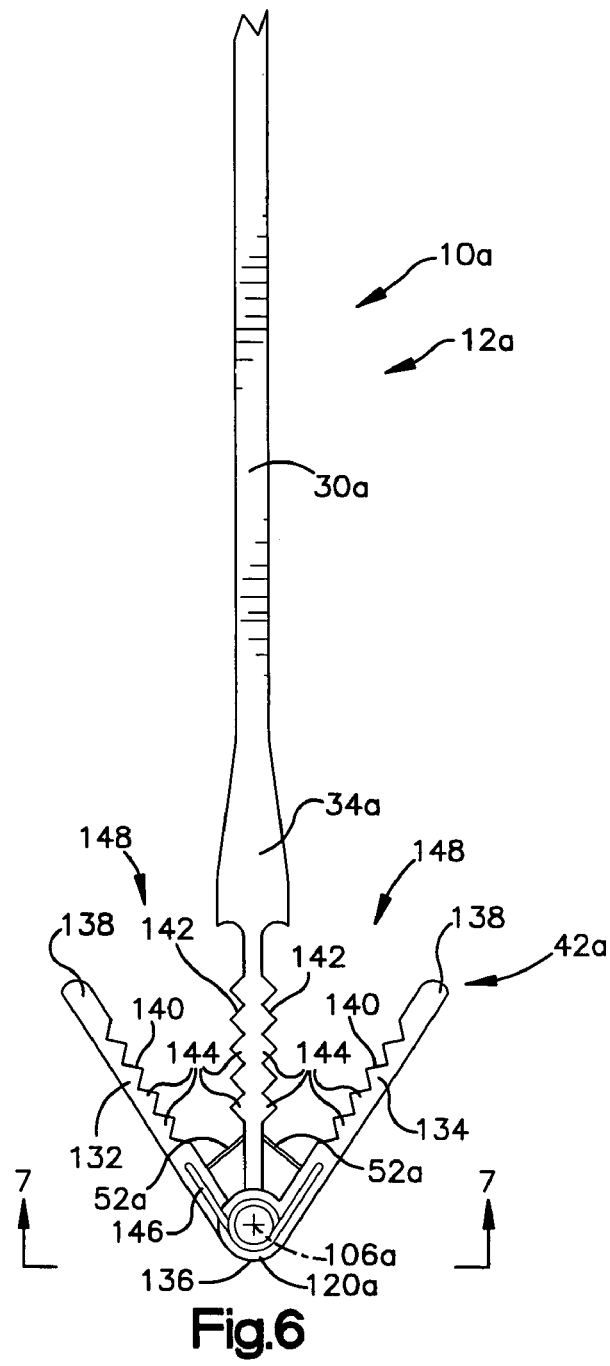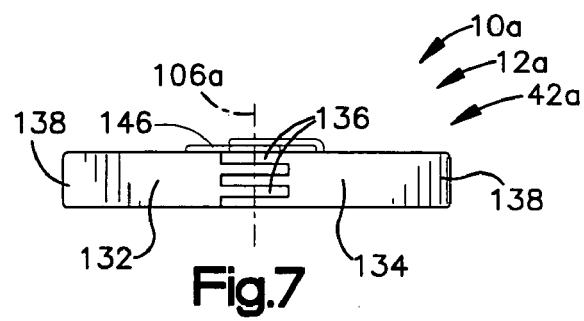

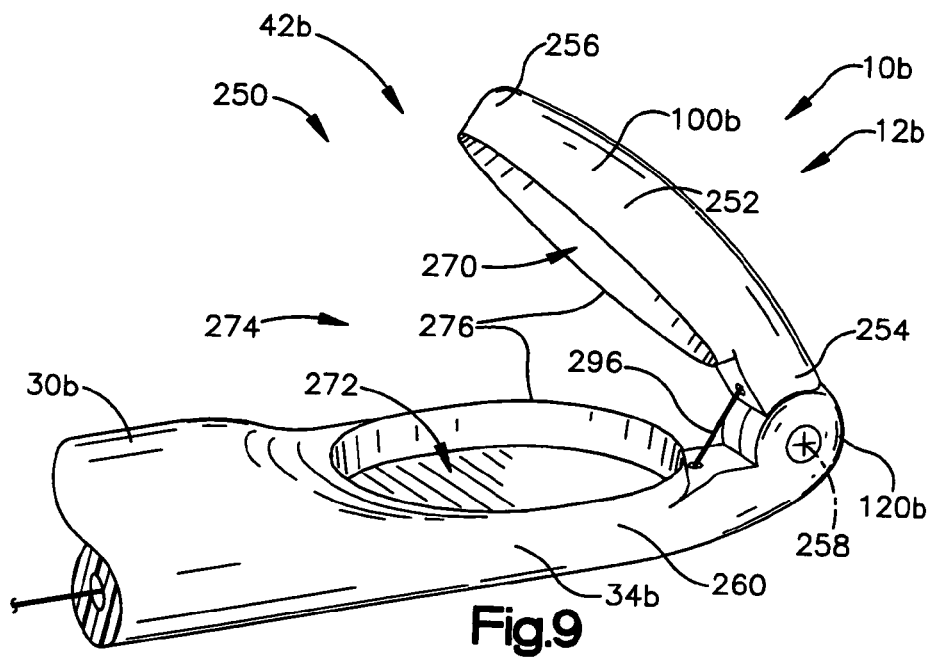
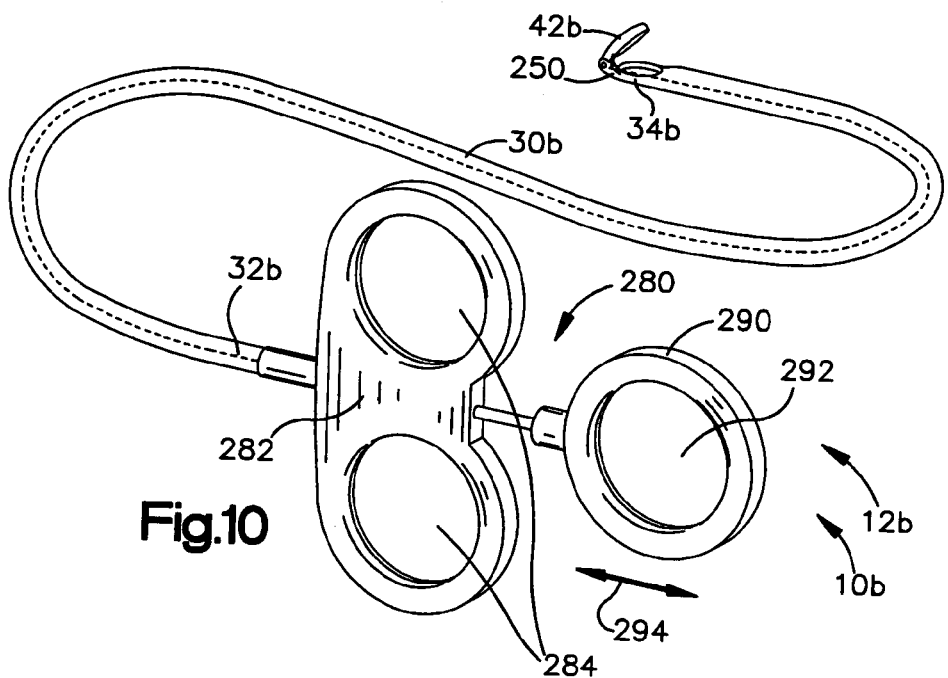
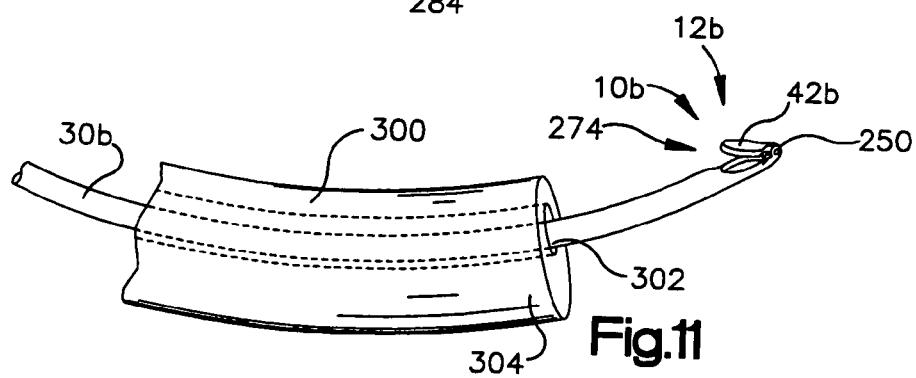

APPARATUS FOR INSERTION INTO A BODY LUMEN

RELATED APPLICATION

This application corresponds to and claims priority from U.S. Provisional Patent Application Ser. No. 60/455,642, filed Mar. 18, 2003, the subject matter of which is incorporated by reference.

BACKGROUND OF THE INVENTION

The present invention relates to an apparatus for insertion into a body lumen. In one embodiment, the present invention relates to an instrument for delivering an implantable device, such as a prosthesis or stent, into a body lumen. The present invention also relates to an instrument for retrieving a foreign object undesirably lodged in a body lumen. The present invention further relates to an instrument for retrieving a tissue sample from within a body lumen.

In one embodiment, the present invention is adapted to deliver stents to body lumens, such as the espohagus. Among other things, these esphogeal stents are used to help relieve dysphagia commonly associated with carcinoma of the esophagus. The esophageal stent is delivered into the esophagus and placed in the affected area. The stent is then expanded radially, which causes dilation of the esophagus and thus helps relieve the dysphagia. Some stents are expanded manually, by means such as a balloon. Other stents have a self-expanding construction.

In another embodiment, the present invention is adapted to perform a biopsy from within a body lumen. In this embodiment, the instrument is inserted into the body lumen and operates to surgically remove a tissue sample from an affected area in the lumen. For example, the present invention may be adapted for use with a bronchoscope to retrieve a biopsy sample from bronchial tubes of a patient.

SUMMARY OF THE INVENTION

The present invention relates to an apparatus for insertion into a body lumen. The apparatus includes an elongate member having a proximal end and a distal end. The distal end is insertable into the body lumen. At least one clamping arm includes a first end having a pivotal connection with the distal end of the elongate member. The pivotal connection provides pivotal movement of the at least one clamping arm relative to the elongate member. The at least one clamping arm extends away from the pivotal connection toward the proximal end of the elongate member. The apparatus also includes a control mechanism for controlling the pivotal movement of the at least one clamping arm relative to the elongate member.

The present invention also relates to an apparatus for insertion into a body lumen. The apparatus includes an elongate member having a proximal end and a distal end. The distal end comprises forceps including at least one clamping arm with a first end having a pivotal connection with the distal end of the elongate member. The at least one clamping arm extends away from the pivotal connection toward the proximal end of the elongate member. The apparatus also includes control means for controlling the pivotal movement of the at least one clamping arm relative to the elongate member.

The present invention also relates to an apparatus for supporting an instrument for insertion into a body lumen. The apparatus includes an outer frame supportable relative to the body lumen and an inner frame connected to the outer frame. The inner frame is rotatable about a first axis relative to the outer frame. The apparatus also includes an advance assembly connected to the inner frame. The advance assembly is pivotable relative to the inner frame about a second axis that extends perpendicular to the first axis. The advance assembly includes a sleeve for receiving the instrument and advancing means operative to impart advancement of the instrument in opposite directions along a longitudinal axis of the instrument.

The present invention further relates to a method for placing a stent within a body lumen. The method includes the step of providing an instrument comprising an elongate member and at least one clamping arm including a first end having a pivotal connection with a distal end of the elongate member. The at least one clamping arm extends away from the pivotal connection toward a proximal end of the elongate member and is actuatable between an open position and a closed position. Next, a radially expandable stent having an inner lumen is provided and slid over the distal end of the elongate member. A leading end of the stent is then clamped between the at least one clamping arm and the elongate member by actuating the at least clamping arm to the closed position. The distal end of the elongate member is then inserted into the body lumen in order to pull the stent clamped thereto to a desired placement location. The at least one clamping arm is then actuated to the open position, which thereby releases the stent for radial expansion into engagement with the body lumen. The distal end is then advanced such that the at least one clamping arm clears the stent. The at least one clamping arm is then actuated back to the closed position and the distal end of the elongate member is removed from the body lumen by pulling the distal end and the at least one clamping arm back through the inner lumen of the stent.

BRIEF DESCRIPTION OF THE DRAWINGS

The foregoing and other features of the invention will become apparent to one skilled in the art to which the invention relates upon consideration of the following description of the invention with reference to the accompanying drawings, in which:

FIG. 2 is a magnified view of a proximal end portion of the apparatus of FIG. 1;

FIG. 3 is a sectional view taken generally along line 3-3 in FIG. 2;

FIG. 4 is a sectional view taken generally along line 4-4 in FIG. 3;

FIG. 5 is a magnified view of a distal end portion of the apparatus of FIG. 1;

FIG. 6 is a magnified schematic illustration of a distal end portion of an apparatus for insertion into a body lumen, according to a second embodiment of the present invention;

FIG. 7 is an end view taken generally along line 7-7 in FIG. 6;

FIG. 9 is a magnified schematic illustration of a portion of an apparatus for insertion into a body lumen, according to a third embodiment of the present invention;

FIG. 10 is a schematic illustration of the apparatus of FIG. 9;

FIG. 11 is a magnified view illustrating an exemplary use of the apparatus of FIG. 10;

DETAILED DESCRIPTION OF THE INVENTION

Figure 1:
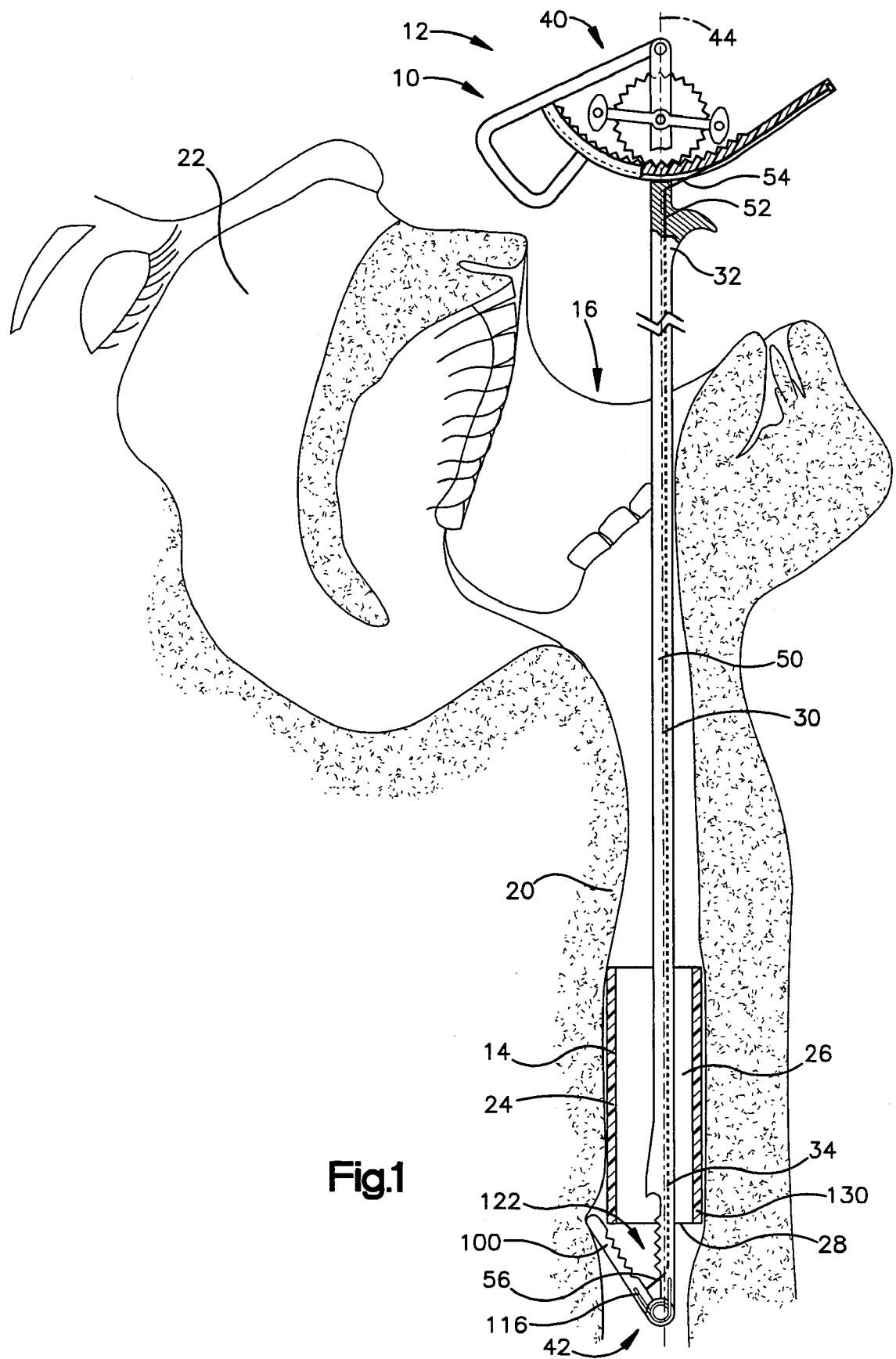
FIG. 1 is a schematic illustration, partially in section, of an apparatus for insertion into a body lumen, according to a first embodiment of the present invention.

The present invention relates to an apparatus for insertion into a body lumen. Referring to FIGS. 1-5, according to a first embodiment of the present invention, the apparatus 10 comprises an instrument 12 for delivering an implantable device 14 (FIG. 1), such as a prosthesis or stent, into a body lumen 16. In the embodiment illustrated in FIG. 1, the body lumen 16 comprises an esophagus 20 of a patient 22. In this embodiment, the device 14 comprises an esophageal stent 24 that is implantable in the esophagus 20. The instrument 12 is adapted for oral delivery of the esophageal stent 24 to the esophagus 20.

The instrument 12 comprises an elongate member in the form of a shaft 30 having a proximal end portion 32 and a distal end portion 34. A control mechanism 40 is connected to or otherwise formed at the proximal end 32 of the shaft 30. A clamping mechanism 42 is connected to or otherwise formed at the distal end 34 of the shaft 30. The shaft 30 has a tubular or hollow construction in which a channel 50 extends along a Longitudinal axis 44 of the shaft from the proximal end 32 to the distal end 34.

A flexible elongated member, such as a wire or cable 52, extends through the channel 50. The cable 52 has a first end 54 operatively connected to the control mechanism 40 and an opposite second end 56 connected to the clamping mechanism 42.

Referring to FIGS. 2-4, the control mechanism 40 includes a bracket 60 that is coextensive with the shaft 30. The control mechanism 40 also includes a cable retractor 62 that is connected to the bracket 60 and pivotable about an axis 64. The first end portion 54 of the cable 52 is connected to the cable retractor 62. The cable retractor 62 has a curved configuration with a grooved surface 66 for receiving the cable 52. The cable retractor 62 also has a toothed surface 68 opposite the grooved surface 66.

The shaft 30 includes a finger rest portion 72 for facilitating handling of the instrument 12. A handle portion 70 of the cable retractor 62 further facilitates handling of the instrument 12. The handle portion 70 also provides a means by which to manipulate the cable retractor 62 to pivot about the axis 64.

The control mechanism 40 also includes a drive gear 80 that is connected to the bracket 60 for rotation about an axis 82. The drive gear 80 has a plurality of gear teeth 84 that engage and mesh with the toothed surface 68 of the cable retractor 62. A handle 86 is operatively connected with the drive gear 80 and rotatable with the drive gear about the axis 82. The handle 86 provides a means by which to impart manually a force for causing the drive gear 80 to rotate about the axis 82.

The control mechanism 40 further includes a ratchet gear 90 that is connected for rotational movement with the drive gear 80 about the axis 82. A pawl 92 is spring biased to engage ratchet teeth 94 of the ratchet gear 90. The pawl 92 blocks rotation of the ratchet gear 90, and thus the drive gear 80, in a first rotational direction about the axis 82 (counterclockwise as viewed in FIG. 4). The pawl permits rotation of the ratchet gear 90 and drive gear 80 in a second rotational direction, opposite the first rotational direction, about the axis 82.

Referring to FIG. 5, the clamping mechanism 42 includes a clamping arm 100 having a first end 102 pivotally connected to the distal end 34 of the shaft 30 and an opposite second end 104. The clamping arm 100 is pivotal relative to the shaft 30 about an axis 106. The clamping arm 100 includes a clamping surface 110 presented toward a clamping surface 112 formed along the distal end 34 of the shaft 30. The clamping surfaces 110 and 112 each include a plurality of teeth 114. The clamping arm 100 together with the portion of the shaft 30 that includes the clamping surface 112 form forceps at the distal end 34 of the shaft.

As shown in FIG. 5, the distal end 34 of the shaft 30 is widened or has an increased diameter compared to the remainder of the shaft. The shaft 30 includes a tapered portion 118 that extends between the widened large diameter portion at the distal end 34 and the narrow smaller diameter portion of the shaft. The tapered portion 118 helps facilitate removal of the instrument 12 from the body lumen 16 by helping to prevent the instrument from snagging or catching onto body tissues in the lumen. Similarly, the second end 104 of the clamping arm 100 has a rounded configuration which helps prevent the arm from snagging or catching onto body tissues in the lumen 16.

In FIG. 5, the clamping arm 100 is illustrated in an open position. In the open position, the clamping surface 110 is spaced from the clamping surface 112. The clamping arm 100 is pivotal about the axis 106 from the open position to a closed position illustrated in dashed lines at 100' in FIG. 5. In the closed position, the clamping surfaces 110 and 112 engage each other and the teeth 110 on the clamping surfaces mesh with each other. A biasing member 116, such as a spring, biases the clamping arm 100 to pivot about the axis 106 toward the open position.

The pivotal connection between the clamping arm 100 and the shaft 30 is located at a terminal end 120 of the distal end portion 34. The clamping arm 100, in the open position, forms an acute angle with the shaft 30 wherein the clamping arm extends in a direction generally toward the proximal end 32 (FIG. 1) and away from the shaft. The clamping arm 100 in the open position thus forms a receptacle 122 for receiving an object, such as the device 14 (i.e., the stent 24). The receptacle 122 faces toward the proximal end 32 of the shaft 30.

In the embodiment illustrated in FIG. 5, a portion of the shaft 30 including the distal end 34 and the clamping portion 42 extends along an axis 124 that is offset from the axis 44 of the shaft 30. This may be desirable, for example, to facilitate insertion of the instrument into a body lumen having a particular shape or configuration. Alternatively, the shaft 30, including the distal end 34, and the clamping portion 42 could extend coaxially along the axis 44 as shown in FIG. 1. As a further alternative, the shaft 30 may be flexible or have a flexible portion or joint that allows for the shaft to be adjusted to a desired shape.

The control mechanism 40 is operable to impart tension on the cable 52. The control mechanism 40 may have any configuration suitable for tensioning the cable 52. One such configuration of the control mechanism 40 is illustrated in FIGS. 1-4. In this configuration, tension is imparted on the cable 52 by urging the cable retractor 62 to pivot about the axis 64 in a counterclockwise direction as viewed in FIG. 2. This can be done either by manipulating the handle portion 70 or by rotating the handle 86. As the cable retractor 62 pivots about the axis 64, the cable 52 is taken-up into the grooved surface 66 of the retractor. As a result, the cable 52 is pulled through the channel 50 (FIG. 1) toward the control mechanism 40.

The spring bias imparted on the clamping arm 100 (FIGS. 1 and 5) by the spring 116 resists the pulling of the cable 52 toward the control mechanism 40. When the force exerted on the cable 52 overcomes the bias of the spring 116, the spring yields and the clamping arm 100 pivots about the axis 106 toward the closed position. The clamping surface 110 moves toward the clamping surface 112, thus closing the receptacle 122 and clamping onto the device 14.

As the cable retractor 62 pivots about the axis 64 to tension the cable 52, the drive gear 80 and the ratchet gear 90 rotate about the axis 82. As the retractor 62 tensions the cable 52, the pawl 92 engages the ratchet teeth 94 to maintain retractor at its current position. This helps maintain tension on the cable 52 and thereby helps maintain the clamping force exerted on the device 14 by the clamping portion 42. The clamping arm 100 is thus "ratcheted" onto the device 14. To release the device 14 from the grasp of the instrument 12, the pawl 92 is disengaged from the ratchet teeth 94 by rotating or pivoting the pawl away from the ratchet gear 90.

Referring to FIG. 1, the cable 52, when tensioned via the control mechanism 40, urges the clamping member 100 towards the closed position. The clamping portion 42 may thus be clamped onto the device 14, i.e., the espohageal stent 24, and the instrument 12 may thus be used to deliver the stent to the esophagus 20 of the patient 22. Similarly, when the stent 24 is delivered to the desired position in the esophagus 20, the control mechanism 40 can be operated to relieve the tension placed on the cable 52 and thus cause the clamping portion 42 to release the stent.

Advantageously, the configuration of the clamping portion 42 allows the device 14 to be pulled, rather than pushed, into the body lumen 16. This is because the clamping arm 100 extends from the distal end 34 toward the proximal end 32 of the shaft 30, i.e., because the receptacle 122 faces the proximal end. The clamping portion 42 may thus clamp onto a leading end 130 of the device 14. By clamping onto the leading end 130, the device 14 may be pulled into position in the body lumen 16. As shown in FIG. 5, the clamping portion 42 includes a hook portion 126 formed adjacent the teeth 114 in the distal end 34 of the shaft 30. The hook portion 126 may hook onto the device 14 and thus aid in pulling the device into position in the body lumen 16.

As shown in FIG. 1, the instrument 12 may be positioned extending through an inner lumen 26 of the stent 24 to position the distal end 34 for clamping onto a leading end 28 of the stent. The instrument 12 could, however, extend outside the stent 24 along an outer surface of the stent and clamp onto the leading end 28 of the stent.

Figure 8:
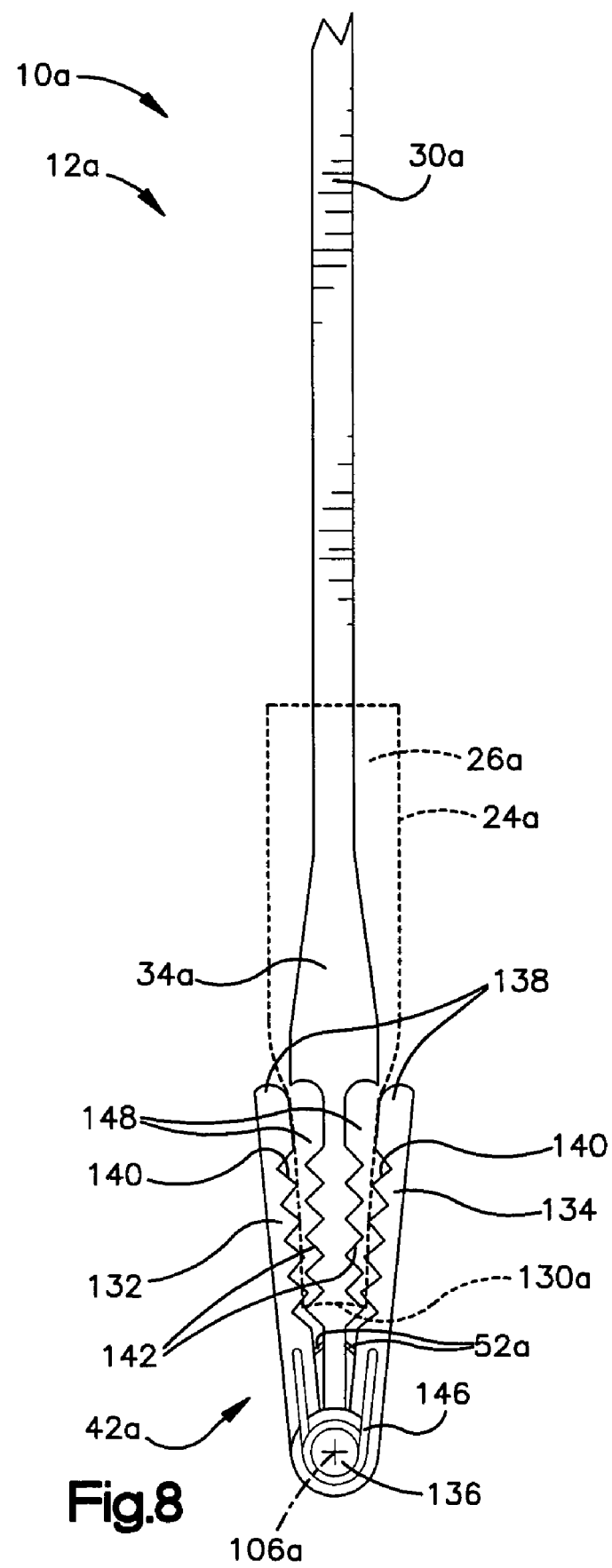
FIG. 8 is a magnified view of the apparatus of FIG. 6, illustrating portions of the apparatus in a closed position.

A second embodiment of the present invention is illustrated in FIGS. 6-8. The second embodiment of the invention is similar to the first embodiment of the invention illustrated in FIGS. 1-5. Accordingly, numerals similar to those of FIGS. 1-5 will be utilized in FIGS. 6-8 to identify similar components, the suffix letter "a" being associated with the numerals of FIGS. 6-8 to avoid confusion. The second embodiment of the present invention is similar to the first embodiment (FIGS. 1-5), except that the clamping mechanism of the second embodiment has a pair of opposed clamping arms instead of a single clamping arm.

Referring to FIGS. 6-8, the apparatus 10a of the second embodiment comprises an instrument 12a having a shaft 30a with a clamping mechanism 42a located at a distal end 34a of the shaft. The clamping mechanism 42a of the second embodiment includes first and second clamping arms 132 and 134, respectively, each having a first end 136 pivotally connected to the distal end 34a of the shaft 30a and an opposite second end 138. The clamping arms 132 and 134 are pivotal relative to the shaft 30a about an axis 106a.

Each of the clamping arms 132 and 134 includes a clamping surface 140 presented toward respective clamping surfaces 142 formed on opposite sides of the distal end 34a of the shaft 30a. The clamping surfaces 140 and 142 each include a plurality of teeth 144. The clamping arms 132 and 134 together with the portions of the shaft 30a that include the clamping surfaces 142 form a pair of forceps on opposite sides of the distal end 34a of the shaft.

FIGS. 6 and 7 illustrate the open position of the clamping arms 132 and 134. In the open position, the clamping surfaces 140 are spaced from their respective clamping surfaces 142. The clamping arms 132 and 134 are pivotal about the axis 106a from the open position to a closed position (see FIG. 8) in which the clamping surfaces 140 and 142 are urged toward each other and toward engagement with each other and the teeth 144 on the clamping surfaces. A biasing member 146 (FIGS. 6-8), such as a spring, biases the clamping arms 132 and 134 to pivot about the axis 106a away from each other and away from the shaft 30a toward the open position.

The pivotal connection between the clamping arms 132 and 134 and the shaft 30a is located at a terminal end 120a of the distal end 34a. The clamping arms 132 and 134, in the open position, form respective acute angles with the shaft 30a wherein the clamping arms extend in a direction generally toward the proximal end (not shown in FIGS. 6-8), upward as viewed in FIG. 6, and away from each other and away from the shaft. The clamping arms 132 and 134 in the open position thus form respective receptacles 148 on opposite sides of the shaft 30a for receiving an object, such as the device (i.e., the espohageal stent). The receptacles 148 face toward the proximal end of the shaft 30a, i.e., generally upward as viewed in FIG. 6.

In the second embodiment, the apparatus 10a may include a control mechanism having a design similar to that of the control mechanism 40 of the first embodiment (see FIGS. 1-4). In operation, such a control mechanism would be effective to tension a cable 52a to actuate the clamping arms 132 and 134 (FIGS. 6 and 8) from the open position to the closed position. As shown in FIG. 6, the cable 52a would have to be split, or two cables provided, in order to actuate both the first and second clamping arms 132 and 134. Also, it will be appreciated that the control mechanism of the second embodiment may be fit with dual control mechanisms that would allow for independent actuation of the first and second clamping arms 132 and 134.

The instrument 12a of the second embodiment is capable of clamping onto and grasping an implantable device at two different locations on the device. The instrument 12a of the second embodiment may also grasp or clamp onto two separate devices. Exemplary of one advantage realized by the dual clamping arms 132 and 134 of the second embodiment, referring to FIG. 8, the instrument 12a may be used to deliver an implantable stent 24a by clamping onto and grasping the stent at two different locations on the stent.

As shown in FIG. 8, the distal end 34a of the instrument 12a is inserted through the inner lumen 26a of the stent 24a. The distal end 34a is passed through the lumen 26a until the clamping mechanism 42a clears the leading end 130a of the stent 24a. The control mechanism is then actuated to place the clamping arms 132 and 134 in the open position. Depending on the configuration of the control mechanism, the clamping arms 132 and 134 may be controlled independently or simultaneously. The instrument 12a is then drawn back through the lumen 26a such that radially opposite portions of the leading end 130a enter the respective receptacles 148 of the clamping mechanism 42a.

Once the portions of the leading end 130a are positioned in the receptacles 148, the control mechanism is actuated to draw the clamping arms 132 and 134 toward the closed position. The leading end 130a of the stent 24a is clamped between the clamping surfaces 140 and 142 and the stent is thereby grasped by the clamping mechanism 42a. By grasping the leading end 130a of the stent 24a, the instrument 12a may be used to pull the stent into a desired position in the body lumen (not shown in FIG. 8).

A third embodiment of the present invention is illustrated in FIGS. 9-11. The third embodiment of the invention is similar to the first embodiment of the invention illustrated in FIGS. 1-5. Accordingly, numerals similar to those of FIGS. 1-5 will be utilized in FIGS. 9-11 to identify similar components, the suffix letter "b" being associated with the numerals of FIGS. 9-11 to avoid confusion. The third embodiment of the present invention is similar to the first embodiment (FIGS. 1-5), except that the clamping mechanism of the third embodiment is adapted to retrieve a biopsy sample from a body lumen.

Referring to FIGS. 9 and 10, the apparatus 10b of the third embodiment comprises an instrument 12b having a shaft 30b with a clamping mechanism 42b located at a distal end 34b of the shaft. The clamping mechanism 42b of the third embodiment comprises cup forceps 250 and includes a clamping arm 100b (FIG. 9) in the form of a first cup portion 252. The first cup portion 252 has a first end 254 pivotally connected to the distal end 34b of the shaft 30b and an opposite second end 256. The first cup portion 252 is pivotal relative to the shaft 30b about an axis 258.

The cup forceps 250 also include a second cup portion 260 connected to, or formed integrally with, the distal end 34b of the shaft 30b. The first cup portion 252 is pivotal about the axis 258 relative to the second cup portion 260 from an open position (FIG. 9) to a closed position (not shown). When the first cup portion 252 is in the open position, the second end 256 is spaced from the second cup portion 260 and the distal end 34b of the shaft 30b. When the first cup portion 252 is in the closed position, the second end 256 is positioned adjacent or against the second cup portion 260 and the distal end 34b of the shaft 30b.

The first and second cup portions 252 and 260 have a generally concave configuration forming respective cup shaped receiving portions 270 and 272. The pivotal connection between the first cup portion 252 and the shaft 30b is located at a terminal end 120b of the distal end portion 34b. The first cup portion 252, in the open position, forms an acute angle with the shaft 30b wherein the first cup portion extends in a direction generally toward the proximal end 32b (FIG. 1) and away from the shaft.

A receptacle 274 is formed between the receiving portions 270 and 272 of the first and second cup portions 252 and 260 when the second cup portion is in the open position of FIG. 11. The receptacle 274 faces toward the proximal end 32b of the shaft 30b. When the second cup portion 260 is in the closed position, the receptacle 274 closes and the receiving portions 270 and 272 form a closed chamber.

The first and second cup portions 252 and 260 each include a peripheral edge or rim that forms a cutting edge 276 extending at least partially about a periphery of its respective receiving portion 270 and 272. One or both of the cutting edges 276 are beveled such that the edges are sharpened for cutting. The cutting edges 276 are presented toward each other such that the edges mate with each other when the second cup portion 256 is in the closed position. The cutting edges 276 may be arranged to engage each other directly to provide a cutting action or may be arranged to pass adjacent to each other to provide a shearing action when the second cup portion 260 is in the closed position.

The shaft 30b may have a rigid construction similar to that shown in the first and second embodiments or may be flexible. Referring to FIG. 10, the instrument 12b is illustrated with a flexible shaft 30b. As shown in FIG. 10, the instrument 12b includes control mechanism 280 positioned at the proximal end 32b of the shaft 30b. The control mechanism 280 of the third embodiment has a configuration that differs from the control mechanism illustrated in FIGS. 1-4. It will be appreciated, however, that either control of these mechanisms, or any other known control mechanism, could be incorporated with the instruments of any of the embodiments disclosed herein.

The control mechanism 280 includes a base 282 with a pair of finger apertures 284 and an actuator 290 that includes a thumb aperture 292. The actuator 290 is movable in an axial direction relative to the base 282 in directions indicated by the arrows labeled 294 in FIG. 10. The actuator 290 is operatively connected with the a clamping mechanism 42b by means such as a cable 296 (see FIG. 9). The base 282 may be grasped with two fingers via the apertures 284 and a thumb may be inserted through the aperture 292 in the actuator 290. This allows for one-handed operation of the control mechanism 280 by moving the thumb relative to the fingers to move the actuator 290 relative to the base 282 in the axial directions 294.

The instrument 12b, including a flexible shaft 30b, is particularly well-suited for use in conjunction with a stereotactic or cannula-type device, such as a bronchoscope. Referring to FIG. 11, the bronchoscope 300 includes an inner lumen 302 into which the cup forceps 250 and the flexible shaft 30b extend. As known in the art, the bronchoscope 300 is insertable orally into a patient (not shown) such that a distal end 304 of the bronchoscope is positioned at a target site, such as a bronchial tube of the patient.

Once the bronchoscope 300 is inserted to the desired position in the patient, the instrument 12b may be inserted into the inner lumen 302 of the scope with the clamping mechanism 42b in the closed position. As shown in FIG. 11, the clamping mechanism 42b at the distal end 34b of the instrument 12b, in this case the cup forceps 250, may thus exit the distal end 304 of the bronchoscope 300, thereby placing the cup forceps at the target site in the bronchial tube.

Once positioned at the target site, the cup forceps 250 may be placed in the open position by actuating the control mechanism 280 (see FIG. 10) in the manner described above. The cup forceps 250 may then be maneuvered such that a biopsy (tissue) sample is positioned in the receptacle 274 of the cup forceps. The cup forceps 250 may then be actuated to the closed position, in which case the cutting edges 276 act to sever the biopsy sample from the patient.

The biopsy sample thus becomes contained in the receptacle 274 formed by the receiving portions 270 and 272 of the first and second cup portions 252 and 260. The biopsy sample may then be removed from the patient by removing the instrument 12b from the bronchoscope 300. Alternatively, the biopsy sample may be removed by removing the bronchoscope 300 and the instrument 12b from the patient simultaneously.

The instruments of the first, second, and third embodiments has been described above for use in delivering and positioning a device in a body lumen. Those skilled in the art, however, will appreciate that the instruments may have alternative uses. For example, the instruments could be used to retrieve an object undesirably lodged in the body lumen. As another example, the instruments may be used to perform surgical operations from within the body lumen. As a further example, the instruments may be adapted to carry a camera (e.g., fiber-optics or other suitable equipment) for viewing inside the body lumen and for aiding in the performance any of the operations described above.

Figure 12:
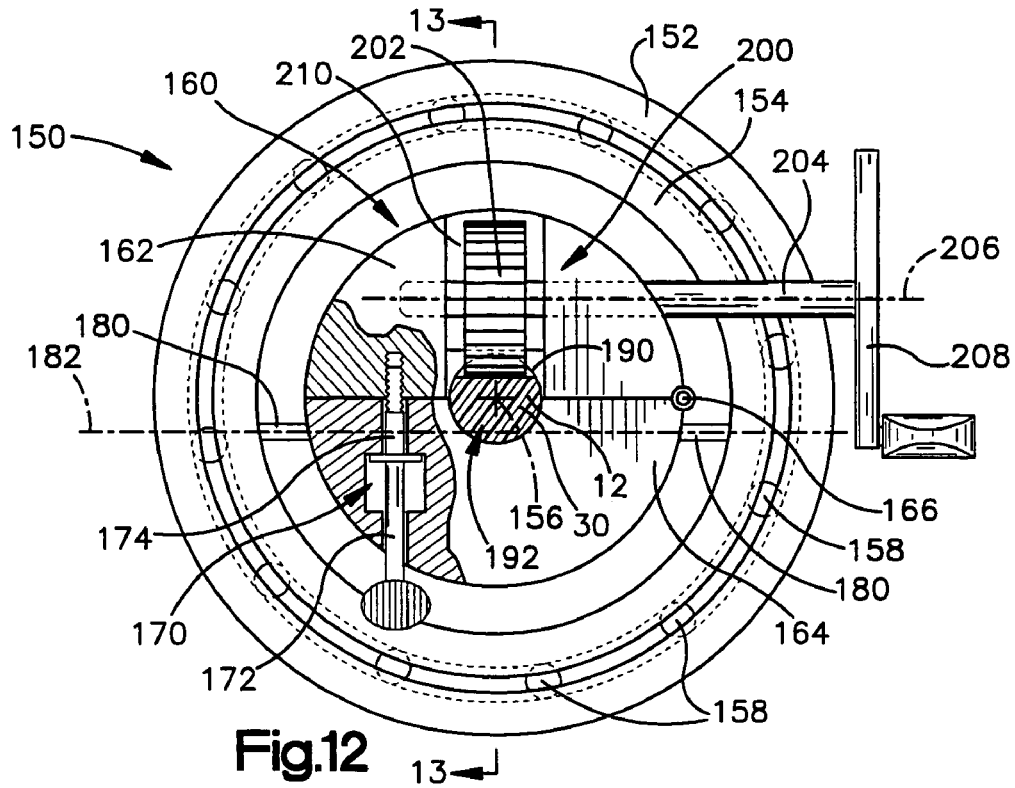
FIG. 12 is a top view of a positioning mechanism for use in conjunction with an apparatus for insertion into a body lumen.
Figure 13:
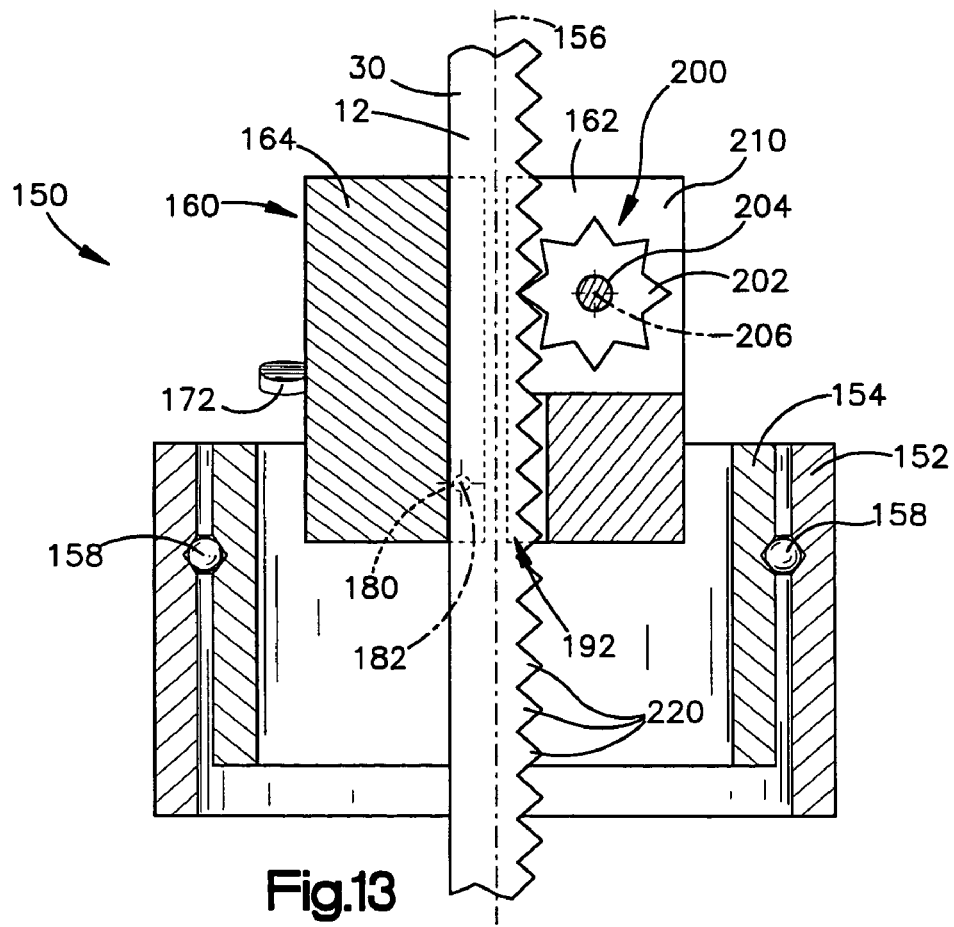
FIG. 13 is a sectional view taken generally along line 13-13 in FIG. 12.

Referring to FIGS. 12 and 13, the apparatus 10 of the first embodiment (FIGS. 1-5), the apparatus 10a of the second embodiment (FIGS. 6-8), or the apparatus 10b of the third embodiment (FIGS. 9 and 10) may include a positioning mechanism 150 for supporting the instrument 12, 12a, 12b and facilitating insertion of the instrument into the body lumen. The positioning mechanism 150 is adapted for use with embodiments of the instrument 12, 12a, 12b that include a rigid shaft.

For simplicity, the positioning mechanism 150 will be described herein as it relates to the apparatus of the first embodiment. The positioning mechanism 150 provides more precise control over the insertion of the instrument 12 into the body lumen as opposed to inserting the instrument in a purely manual manner, i.e., "by hand."

The positioning mechanism 150 may have any configuration suitable for positioning the instrument 12 in the manner that will be described below. Illustrative of one such configuration, referring to FIGS. 11 and 12, the positioning mechanism 150 includes a generally cylindrical ring-shaped outer frame 152 that supports a generally cylindrical ring-shaped inner frame 154. The inner frame 154 has a diameter smaller than a diameter of the outer frame 152. The outer and inner frames 152 and 154 are arranged concentrically with each other on an axis 156. A plurality of bearings 158 are disposed in an annular arrangement between the outer frame 152 and inner frame 154. The bearings 158 support the inner frame 154 for rotation about the axis 156 relative to the outer frame 152.

The positioning mechanism 150 also includes an advance assembly 160 supported in the cylindrical area defined by the inner frame 154. The advance assembly 160 includes first and second clamping members 162 and 164, respectively, connected to each other by a hinge 166. The first and second clamping members 162 and 164 each have a generally semi-cylindrical configuration. The first and second clamping members 162 and 164 are thus pivotable about the hinge 166 away from each other to an advancing position illustrated in FIG. 12, and toward each other to a clamping position illustrated in FIG. 11. In the clamped position, the first and second clamping members 162 and 164 assume a generally cylindrical configuration and are centered on the axis 156.

A locking assembly 170 includes a thumb screw 172 and a stop bushing 174. The thumb screw 172 has a threaded screw portion that cooperates with threads in the first clamping member 162 to draw the clamping members toward each other or urge the clamping members away from each other. The locking assembly 170 is thus operable to actuate the first and second clamping members 162 and 164 between the advancing position and the clamping position.

The advance assembly 160 is connected to the inner frame 154 by a pair of pins 180 aligned on an axis 182. The pins 180 allow for pivotal movement of the advance assembly 160 about the axis 182 relative to the inner frame 154. The axis 182 extends generally perpendicular to the axis 156. The pins 180 may also allow for the detaching of the advance assembly 160 from the inner frame 154. For example, the pins 180 may be fixed to the advance assembly 160 and may "snap" into semi-cylindrical grooves (not shown) in the inner frame 154.

The first and second clamping members 162 and 164 each include a semi-cylindrical recess 190 presented toward each other along mating edges of the clamping members. When the clamping members 162 and 164 are in the clamping position, the recesses 190 combine to form a cylindrical sleeve 192 extending through the clamping members. The sleeve 192 is centered on the axis 156.

The advance assembly 160 also includes an advance mechanism 200 supported by the first clamping member 162. The advance mechanism 200 includes a pinion gear 202 supported in a recess 210 in the first clamping member 162. The pinion gear 202 is supported on a shaft 204 for rotation about an axis 206. A handle 208 connected with the shaft 204 provides a means by which to impart rotational movement of the shaft and the gear 202.

The cylindrical sleeve 192 is sized to receive the shaft 30 of the instrument 12. Detaching the advance assembly 160 from the inner frame 154 allows the clamping members 162 and 164 to pivot about the hinge 166 so that the shaft 30 may be placed within the opposing recesses 190. The clamping members 162 and 164 may then be closed to enclose the shaft 30 within the sleeve 192 and thereby connect the instrument 12 to the advance assembly 160. The advance assembly 160, with the instrument 12 connected thereto, may then be snapped back into the inner frame member 154.

As best shown in FIG. 13, the shaft 30 includes a series of rack teeth 220 disposed along the length shaft. When the instrument 12 is supported in the advance assembly 160, the rack teeth 220 are presented toward the pinion gear 202 and mesh with the gear teeth on the pinion gear.

In preparing the positioning device 150 for operation, the positioning device is fixed in a position relative to the body lumen of the patient. This may be done by clamping or otherwise supporting the outer frame 152 to a support structure, such as an operating table, by means such as a clamp or frame (not shown). Such a clamp or frame would have an articulated construction such that the positioning device may be positioned in a desired location relative to the patient. The positioning device 150, when fixed in a desired position relative to the body lumen of the patient, is operable to help control or adjust the position of the instrument 12 relative to the body lumen/patient.

The positioning device 150 can be used to adjust the orientation of the instrument 12 relative to the body lumen. The instrument 12 can be rotated about the axis 156 by rotating the advance assembly 160 and the inner frame 154 relative to the outer frame 152. The instrument can be pivoted about the axis 182 by pivoting the advance assembly 160 relative to the inner frame 154. The inner frame 154 can be rotated about the axis 156 and/or the advance assembly 160 can be pivoted about the axis 182 in any combination required to achieve the desired orientation of the instrument 12. The positioning device 150 may include means (not shown) for locking the inner frame 154 against rotation relative to the outer frame 152, and for locking the advance assembly 160 against pivoting relative to the inner frame. The positioning device 150 may thus be locked to maintain a desired orientation of the instrument 12.

The advance position of the instrument 12 relates to the position of the instrument in the body lumen, as measured along the axis 156. An increase in the advance position is achieved by inserting the instrument 12 further into the body lumen. A decrease in the advance position of the instrument 12 is achieved by retracting the instrument out of the body lumen. The advance position of the instrument 12 can be adjusted via the advance assembly 160.

To adjust the advance position of the instrument 12, the locking assembly 170 is actuated via the thumb screw 172 to place the clamping members 162 and 164 in the advancing position. The handle 208 can then turned to cause rotation of the pinion gear 202 in order to effectuate an adjustment, either positive or negative, in the advance position of the instrument 12. Once the instrument 12 is in the desired advance position, the locking assembly 170 is actuated via the thumb screw 172 to place the clamping members 162 and 164 in the clamped position. In the clamped position, the clamping members 162 and 164 exert a clamping force on the shaft 30, which helps prevent the advance position of the instrument 12 from changing inadvertently.

Referring back to FIG. 1, those skilled in the art will thus appreciate that the present invention also relates to a method for placing a stent 24 within a body lumen 16. The method includes the step of providing an instrument 12 comprising an elongate member 30, at least one clamping arm 100 pivotably mounted at a distal end 34 of the elongate member, and control means 40 for controlling the pivotable movement of the at least one clamping arm between an open position and a closed position. The method also includes the step of providing a radially expandable stent 24 having an inner lumen and sliding the stent over the distal end 34 of the elongate member 30. Next, a leading end 130 of the stent 24 is clamped between the at least one clamping arm 100 and the elongate member 30 by moving the at least clamping arm to the closed position. The method also includes the step of inserting the distal end 34 of the elongate member 30 into the body lumen 16 and pulling the stent 24 clamped thereto to a desired placement location. The at least one clamping arm 100 is pivoted to the open position using the control means 40, which thereby releases the stent 24 for radial expansion into engagement with the body lumen. The instrument 12 is then advanced slightly such that the clamping arm 100 clears the stent 24. The at least one clamping arm 100 is then moved back to the closed position using the control means 40, and the distal end 34 of the elongate member is removed from the body lumen 16 by pulling the distal end and the at least one clamping arm 100 back through the inner lumen of the stent 24.

The step of clamping the stent 24 between the at least one clamping arm 100 and the elongate member 30 may comprise the step of moving a mechanism 62 (FIG. 2) located at a proximal end 32 of the elongate member 30. The mechanism and 62 a connecting member 52 forming the control means 40. The connecting member 52 extends between the mechanism 62 and the at least one clamping arm 100.

The step of clamping the stent between the at least one clamping arm 100 and the elongate member 30 may also comprise the step of pivoting the at least one clamping arm to its open position using the control means 40. Then, the stent 24 is slid distally into a receptacle 122 formed at the distal end 34 of the elongate member 30 by the at least one clamping arm 100 in its open position. Then, the at least one clamping arm 100 is pivoted to its closed position using the control means 40, thereby clamping the stent 24 between the at least one clamping arm and the elongate member 30.

From the above description of the invention, those skilled in the art will perceive improvements, changes and modifications in the invention. For example, the instruments of the first and second embodiments may be fit with the flexible shaft and control mechanism of the third embodiment. Further, it is contemplated that the inventive instruments disclosed herein could be made smaller and without teeth so that they could be used as a hemostat during surgery. Such improvements, changes and modifications within the skill of the art are intended to be covered by the appended claims.

Having described the invention, I claim:

1. An apparatus for insertion into a body lumen, said apparatus comprising:
    an elongate member having proximal and distal ends, said distal end being insertable into the body lumen;
    at least one clamping arm including a first end having a pivotal connection with said distal end of said elongate member, said pivotal connection providing pivotal movement of said at least one clamping arm relative to said elongate member, said at least one clamping arm extending away from said pivotal connection toward said proximal end of said elongate member;
    control means for controlling the pivotal movement of said at least one clamping arm relative to said elongate member, said control means being operatively connected with said at least one clamping arm; and
    a positioning mechanism for supporting said elongate member and facilitating insertion of said elongate member into the body lumen, said positioning mechanism comprising:
        an outer frame supportable relative to the body lumen;
        an inner frame connected to said outer frame, said inner frame being rotatable about a first axis relative to said outer frame; and
        an advance assembly connected to said inner frame, said advance assembly being pivotable about a second axis relative to said inner frame, said second axis extending perpendicular to said first axis, said advance assembly comprising a sleeve for receiving said elongate member and advancing means operative to impart advancement of said elongate member in opposite directions along a longitudinal axis of said elongate member.

2. The apparatus of claim 1 wherein said advance assembly further comprises first and second clamping members that form said sleeve for receiving said elongate member, said advance assembly further comprising a locking mechanism operative to place said advance assembly in a locked condition wherein said clamping members clamp onto said elongate member to fix the position of said elongate member relative to said advance assembly, said locking mechanism being further operable to place said advance assembly in an advancing condition wherein said elongate member is released for movement relative to said advance assembly along said longitudinal axis of said elongate member.

3. The apparatus of claim 1 wherein said advancing means comprises a rack and pinion gear set for imparting movement of said elongate member along said longitudinal axis, said rack and pinion gear set comprising a series of rack teeth arranged along an outer surface of said elongate member and a pinion gear having teeth meshingly engaged with said rack teeth, said pinion gear being rotatable to impart movement of said elongate member along said longitudinal axis.

* * * * *